United States Patent [19]

Buynak et al.

[11] 4,145,252
[45] Mar. 20, 1979

[54] RESPIRATORY SYNCYTIAL VACCINE

[75] Inventors: Eugene B. Buynak, North Wales; Maurice R. Hilleman, Lafayette Hill, both of Pa.

[73] Assignee: Merck & Co., Inc., Rahway, N.J.

[21] Appl. No.: 918,760

[22] Filed: Jun. 26, 1978

Related U.S. Application Data

[60] Division of Ser. No. 825,520, Aug. 17, 1977, which is a continuation-in-part of Ser. No. 766,995, Feb. 9, 1977, abandoned.

[51] Int. Cl.$^2$ ................................................ C12K 7/00
[52] U.S. Cl. ..................................................... 195/1.3
[58] Field of Search .......................................... 195/1.3

[56] References Cited

PUBLICATIONS

Law et al., Chem. Abst., vol. 69 (1968) p. 65374u.
Friedewald et al., J. of American Med. Assn., vol. 204, May 20, 1968, pp. 690–694.
Kim et al., Pediatrics, vol. 48, Nov. 1971, pp. 745–755.
McIntosh et al., Pediatric Research, vol. 8 (1974), pp. 689–696.
Wright et al., J. of Pediatrics, vol. 88, Jun. 1976, pp. 931–936.

Primary Examiner—Sam Rosen
Attorney, Agent, or Firm—Donald J. Perrella; Julian S. Levitt

[57] ABSTRACT

By serially passaging virulent respiratory syncytial virus in human diploid lung fibroblasts, a non-pathogenic but antigenic live respiratory syncytial virus is produced. This virus is useful in preparing a live virus vaccine.

6 Claims, No Drawings

RESPIRATORY SYNCYTIAL VACCINE

RELATED APPLICATIONS

This application is a division of copending application Ser. No. 825,520 filed Aug. 17, 1977 which is a continuation-in-part of copending application Ser. No. 766,995 filed Feb. 9, 1977, now abandoned.

BACKGROUND OF THE INVENTION

1. Field of the Invention

This invention relates to a vaccine for respiratory syncytial virus and to a method for producing the vaccine.

Respiratory syncytial virus, discovered in 1956, is worldwide in distribution but unfamiliar to most patients. It is an important cause of respiratory tract illness in infants and young children. In infants this severe illness often requires hospitalization and is considered a cause of sudden infant death syndrome. About 30 percent of hospitalized yound children with acute respiratory disease have respiratory syncytial virus infection. In older children and adults the disease is milder. Infections with respiratory syncytial virus are referable to all segments of the respiratory tract, are usually associated with fever, cough, runny nose, and fatigue, and are diagnosed clinically as bronchitis, bronchiolitis, pneumonia, croup, or viral infection. In older children and adults tne virus is limited in growth in the upper respiratory tract. Infants may be more severely involved when the virus extends into the lungs.

Primary infection with respiratory syncytial virus occurs early in life, usually before four years of age. Among children, illness caused by this virus tends to occur at least once each year in rather sharply defined outbreaks of several months duration. Epidemics are sharply circumscribed, generally for three to five months. In family studies, children in early school years frequently introduce the virus into the home, infecting younger members of the family more severely than other family members. The clinical consequence of infection is most severe on first experience and becomes milder in older individuals who are immunologically experienced.

The effects of respiratory syncytial virus can range from inapparent infection to severe pneumonia and death. Inflamation of the respiratory tract is responsible for most symptoms. Complete recovery in most cases occurs in one to three weeks with the production of protective antibody which appears to persist throughout life. In the United States about 30 percent of one-year old infants and 95 percent of five-year old children have circulating respiratory syncytial virus antibody. Reinfections in older infants, children, and adults with antibody are mostly mild upper respiratory illnesses in the form of colds.

2. Description of the Prior Art

Friedewald et al., Journal of the American Medical Association, Vol. 204, 20 May 1968, pp. 690-694 describe the propagation of respiratory syncytial virus in bovine embryonic kidney tissue culture. Virus grown at 34° C. or 28° C. did not decrease in infectivity or virulence. Virus grown at 26° C., however, while associated with a decrease in infectivity for adults, could not be considered for use in prevention of infection in adults since the virus had limited infectivity and was poorly immunogenic. The effect on the young of virus grown at 26° C. was not determined.

Kim et al., Pediatrics, Vol. 48, November 1971, pp. 745-755, disclose that inactivated respiratory syncytial virus vaccine prepared from virus grown at 26° C. stimulated the development of high levels of serum antibody in infants and children from 6 months to 13 years in age but did not prevent infection.

McIntosh et al., Pediatric Research, Vol. 8, 1974, pp. 689-696, discuss two experimental live respiratory syncytial virus vaccines, one prepared from virus grown at 26° C. and the other, prepared from a temperature sensitive mutant which grew well at 32° C. and not at all at 37° C. or higher. The first vaccine was unsatisfactory as it did not protect against infection when the interval between vaccination and challenge was greater than 4 months. The second vaccine was also unsatisfactory in that it apparently lost its temperature sensitivity in some vaccinees.

Craighead, Journal of Infectious Diseases, Vol. 131, June 1975, pp. 749-753, discusses tests conducted in 1966 wherein several groups of investigators tested in infants and young children a formaldehyde-treated, alum-precipitated virus grown in tissue culture. Upon subsequent exposure to wild virus the vaccine recipients exhibited an accentuated pattern of respiratory tract disease. Craighead concludes that immunization enhanced the severity of the disease.

Wright et al., Journal of Pediatrics, Vol. 88, June 1976, pp. 931-936, describe the evaluation in infants of a temperature sensitive live attenuated respiratory syncytial vaccine. While this vaccine when administered at a dosage level sufficiently high to infect all seronegative infants caused mild upper respiratory illness, lowering the dose did not achieve an acceptable level of infectivity. The virus was also genetically unstable as there was evidence of loss of temperature sensitivity in one vaccinee. While there was no evidence for potentiation of natural illness of this vaccine, reinfection occurred among vaccinees.

OBJECTS OF THE INVENTION

It is, accordingly, an object of the present invention to provide a safe, effective respiratory syncytial virus vaccine. Another object is to provide a respiratory syncytial virus vaccine which is antigenic while non-pathogenic. A further object is to provide a respiratory syncytial virus vaccine which protects against the effects of this virus on both initial and subsequent challenge. Still another object is to provide physiologically acceptable compositions for administering respiratory syncytial virus vaccine. Yet another object is to provide a method for attenuating respiratory syncytial virus. Another object is to provide a method for preparing a respiratory syncytial virus vaccine. These and other objects of the present invention will be apparent from the following description.

SUMMARY OF THE INVENTION

It has now been found that a non-pathogenic but antigenic live respiratory syncytial virus is produced by serially passaging virulent respiratory syncytial virus from about 3 to about 30 passages in human diploid lung fibroblasts at a temperature of from about 30 to about 38° C.

DETAILED DESCRIPTION

In general terms, the invention is concerned with the adaption and propagation of respiratory syncytial virus in human diploid lung fibroblasts. More particularly this invention is directed to the development of a live attenuated respiratory syncytial virus vaccine following serial passage in human diploid lung fibroblasts. The WI-38 fibroblasts, originally derived from a singly human lung, have been extensively characterized biologically, biochemically, virologically, and genetically. Likewise, the MRC-5 fibroblasts, also derived from a singly human lung but from a different individual, are also standardized. WI-38 fibroblasts are described in Exper. Cell Res. 25, 585 (1961) and are deposited with the American Type Culture Collection (ATCC CCL-75). MRC-5 fibroblasts are described in Nature 227, 168, (July 11, 1970). Propagation of human diploid lung fibroblasts may be carried out by any of the standard methods described in the literature. For example, human diploid lung fibroblasts are prepared in glass bottles using BME (GIB-Diploid) supplemented with 10 percent unheated calft serum as growth medium. Following incubation at 36° C. for 48–72 hours cultures can be used for serial passage or vaccine preparation.

The procedure of the present invention involves the steps of A) the isolation of the virulent virus in any of a variety of cells in culture, and its adaption to human diploid lung fibroblasts; B) the development of the attenuated live virus by a plurality of serial passages in human diploid lung fibroblasts; and C) the preparation of the vaccine from this attenuated live virus. These steps will be separately explained.

A. Isolation and adaptation of virulent virus

Isolation and adaptation of respiratory syncytial virus can be accomplished in human diploid lung fibroblasts using virus previously propagated in known manner in another kind of cell culture, such as for example, monkey kidney. Isolation in cell culture such as, e.g. monkey kidney, can be from clinical material (e.g., throat swab). Isolation may be carried out by one or more serial passages in such cell culture. After isolation the virus is subjected to from about 3 to about 30 serial passages, preferably from about 4 to about 15 serial passages in human diploid lung fibroblasts. These passages serve to adapt and attenuate the virus. Incubation of infected cultures in human diploid lung fibroblasts can be carried out at any temperature between about 30° C. and about 38° C., preferably from about 30° to about 34° C. (optimally about 32° C.), or from about 35° to about 38° C. (optimally about 36° C.).

B. Development of attenuated live respiratory syncytial vaccine

The virus which has been isolated and adapted as described in A is added to glass bottles containing human diploid lung fibroblasts. The culture medium may be any of those which supports cell growth and this may be, for example, the known Eagle's basal medium (BME) or Eagle's minimal essential medium (MEM) in Eagle's balanced salt solution (BSS) supplemented with pre-screened calf serum. After the additon of the virus, the infected cell cultures are incubated in successive passages at from about 30° to about 38° C. a number of times effective to attenuate the virus yet retain its antigenicity and immunogenicity. Generally, from about 3 to about 30 successive passages at from about 30° to about 38° C. and preferably at from about 30° to about 34° C. (optimally about 32° C.) or from about 35° to about 38° C. (optimally about 36° C.) are required. Preferably the virus is incubated in from about 4 to about 15 successive passages. During these passages the virus is replicated in large amount and becomes attenuated.

The above serial passages are performed using undiluted or diluted inoculum and multiple harvests are collected at various intervals. Titrations are performed in HEP-2 cell cultures, either in tubes or Falcon microtiter plates.

The harvested virus is then stored frozen or at low temperature to preserve its potency. Prior to freezing a suitable stabilizer or a combination of suitable stabilizers such as, for example, sorbitol or gelatin is added in appropriate amounts as determined from stability tests on frozen and lyophilized viral product.

C. Preparation of vaccine from attenuated virus

The respiratory syncytial virus harvested after repeated serial passages, typically from about 3 to about 30 passages, is found to be nonpathogenic for monkeys and rodents, to cause little or no clinical reactions in human recipients, and to evoke a satisfactory level of neutralizing antibody. After titration to establish its potency, the virus pool is subdivided and filled into appropriate vials for use. The product can be stored frozen or preferably dried from the frozen state and kept free of moisture.

The following examples illustrate the present invention without, however, limiting the same thereto.

EXAMPLE 1

The Merck strain (287) of respiratory syncytial virus, used in the preparation of the attenuated live virus vaccine was isolated from a throat swab specimen (received from Dr. R. Chanock, National Institute of Allergy and Infectious Diseases, National Institute of Health). This initial inoculum is subjected to two passages in monkey kidney cell culture and four passages in WI-38 human diploid lung fibroblasts. The WI-38 human diploid lung fibroblasts are prepared in glass bottles using BME supplemented with 10 percent unheated fetal calf serum as growth medium. Two days post-planting the growth medium is decanted, and the cultures inoculated with 5.0 ml of undiluted fourth passage seed virus per bottle (diluted seed virus may be used if desired). Following an adsorption period of one hour at 30°–34° C., 100 milliliters of MEM containing 2 percent unheated fetal calf serum are added to each bottle, and re-incubated at 30°–34° C. Three to four days post-seeding, the bottle cultures are washed four times with Hank's BSS, 100 milliliters per wash. Following the washing procedure, 100 milliliters of MEM containing a suitable viral stabilizer, e.g., human albumin is added to each bottle and the cultures incubated at 30°–34° C. Neomycin at a concentration of 50 mcg/ml is incorporated in the growth and maintenance medium. Multiple harvests are collected at 2–4 day intervals and the bottle cultures are refed with fresh maintenance medium containing stabilizer. A viral stabilizer consisting of a mixture of equal parts of sorbitol and gelatin is added prior to shell freezing and storage at −70° C. (electrically operated). One or more appropriate harvests are selected following completion of infectivity titrations. The selected material is removed from the freezer and thawed. A sample is removed for control and safety testing. The remaining fluid is clarified and a sample removed for monkey safety testing. The fluids are distributed into individual vials and lyophilized. Following the lyophilization cycle, the vials are capped, sealed, and retained for reconstitution as a vaccine by the addition of sterile water (Water for Injection, U.S.P.).

The potency of the product is based on infectivity titration in HEP-2 cell culture.

EXAMPLE 2

The procedure of Example 1 is repeated except that nine serial passages in WI-38 human diploid fibroblasts are employed rather than four.

EXAMPLE 3

The procedure of Example 1 is repeated except that the incubation temperature of respiratory syncytial virus is in the 35°–38° C. range rather than 30°–34° C.

EXAMPLE 4

Eight children without previous respiratory syncytial virus infection were administered a dose of the attenuated respiratory syncytial virus vaccine of Example 1 by the parenteral route. Essentially all of these developed a significant level of neutralizing antibody within six weeks after vaccination. There were no untoward clinical reactions.

EXAMPLE 5

Eleven children without previous respiratory syncytial virus infection were administered a dose of the attenuated respiratory syncytial virus vaccine of Example 2 by the parenteral route. Essentially all of these developed a significant level of neutralizing antibody within six weeks after vaccination. There were no untoward clinical reactions.

EXAMPLE 6

Samples of viruses prepared as described in Examples 1 and 2 are frozen and stored at −70° C. for over 18 months. On thawing the potency of the samples is found to be essentially unchanged.

EXAMPLE 7

Samples of viruses prepared as described in Examples 1 and 2 are lyophilized and stored at −20° C. for over 18 months. On reconstitution the potency of the samples is found to be essentially unchanged.

What is claimed is:

1. A process of preparing an attenuated respiratory syncytial virus comprising serially passaging a respiratory syncytial virus in human dipoid lung fibroblasts at an incubation temperature of from about 30° to about 38° C. for a number of passages effective to attenuate the virus yet retain its antigenicity and immunogenicity, and harvesting the resulting virus.

2. A process according to claim 1 wherein from about 3 to about 30 serial passages are employed.

3. A process according to claim 1 wherein from about 4 to about 15 serial passages are employed.

4. A process according to claim 1 wherein the human diploid lung fibroblasts are WI-38 fibroblasts.

5. A process according to claim 1 in which the incubation is carried out at from about 30° to about 34° C.

6. A process according to claim 1 in which the incubation is carried out at from about 35° to about 38° C.

* * * * *